(12) United States Patent
Krulevitch et al.

(10) Patent No.: US 6,352,838 B1
(45) Date of Patent: Mar. 5, 2002

(54) MICROFLUIDIC DNA SAMPLE PREPARATION METHOD AND DEVICE

(75) Inventors: Peter A. Krulevitch, Pleasanton; Robin R. Miles, Danville; Xiao-Bo Wang, San Diego; Raymond P. Mariella, Danville, all of CA (US); Peter R. C. Gascoyne, Bellaire, TX (US); Joseph W. Balch, Livermore, CA (US)

(73) Assignee: The Regents of the Universtiy of California, Oakland, CA (US)

( * ) Notice: Subject to any disclaimer, the term of this patent is extended or adjusted under 35 U.S.C. 154(b) by 0 days.

(21) Appl. No.: 09/545,150

(22) Filed: Apr. 7, 2000

Related U.S. Application Data

(60) Provisional application No. 60/128,127, filed on Apr. 7, 1999.

(51) Int. Cl.[7] .................................................. C12A 1/68
(52) U.S. Cl. ................. 435/34; 435/252.31; 435/306.1; 435/261; 435/308.1; 204/547; 204/643; 536/23.1
(58) Field of Search .............................. 435/306.1, 261, 435/308.1, 252.31, 34; 204/547, 643; 536/23.1

(56) References Cited

U.S. PATENT DOCUMENTS

| | | | |
|---|---|---|---|
| 4,305,797 A | 12/1981 | Knoll et al. | 204/108 R |
| 4,390,403 A | 6/1983 | Batchelder | 204/108 R |
| 4,476,004 A | 10/1984 | Pohl | 204/299 R |
| 4,822,470 A | 4/1989 | Chang | 204/299 R |
| 4,970,154 A | 11/1990 | Chang | 435/172.2 |
| 5,304,486 A | 4/1994 | Chang | 435/287 |
| 5,489,506 A | 2/1996 | Crane | 435/2 |
| 5,569,367 A | * 10/1996 | Betts et al. | 204/547 |
| 5,795,457 A | 8/1998 | Pethig et al. | 204/547 |
| 5,814,200 A | 9/1998 | Pethig et al. | 204/547 |
| 5,858,192 A | 1/1999 | Becker et al. | 204/547 |
| 5,929,208 A | * 7/1999 | Heller et al. | 530/333 |
| 5,993,630 A | * 11/1999 | Becker et al. | 204/547 |

* cited by examiner

*Primary Examiner*—James Ketter
(74) *Attorney, Agent, or Firm*—Alan H. Thompson

(57) ABSTRACT

Manipulation of DNA molecules in solution has become an essential aspect of genetic analyses used for biomedical assays, the identification of hazardous bacterial agents, and in decoding the human genome. Currently, most of the steps involved in preparing a DNA sample for analysis are performed manually and are time, labor, and equipment intensive. These steps include extraction of the DNA from spores or cells, separation of the DNA from other particles and molecules in the solution (e.g. dust, smoke, cell/spore debris, and proteins), and separation of the DNA itself into strands of specific lengths. Dielectrophoresis (DEP), a phenomenon whereby polarizable particles move in response to a gradient in electric field, can be used to manipulate and separate DNA in an automated fashion, considerably reducing the time and expense involved in DNA analyses, as well as allowing for the miniaturization of DNA analysis instruments. These applications include direct transport of DNA, trapping of DNA to allow for its separation from other particles or molecules in the solution, and the separation of DNA into strands of varying lengths.

20 Claims, 4 Drawing Sheets

FIG. 1

AEROSOL COLLECTION (11) → ORGANIC/INORGANIC SEPARATION (13) → DISRUPTION (15) → DNA EXTRACTION (17) → MIX WITH REAGENTS (19) → ASSAY (21)

MICROFLUIDIC DNA SAMPLE PREPARATION METHOD AND DEVICE

CROSS REFERENCE TO RELATED APPLICATIONS

This invention claims the benefit of a priority date of Apr. 7, 1999 based on a U.S. provisional patent application No. 60/128,127, entitled "Applications of Dielectrophoresis to DNA Sample Preparation."

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to an integrated microelectromechanical system (MEMS) method of trapping and collecting a biological sample, processing the sample, and analyzing the result to detect and identify the sample. The invention is useful for the detection of biological warfare agents, hazardous bacteria in agricultural products and prepared food, genetic-based biomedical assays, and mapping DNA of the human genome.

2. Description of Related Art

Dielectrophoresis (DEP)has been used very successfully by researchers at the University of Texas MD Anderson Cancer Center to separate various types of cells, such as cancerous from non-cancerous cells [F. F. Becker, X.-B. Wang, Y. Huang, R. Pethig, J. Vykoukal, and P. R. C. Gascoyne, "The Removal of Human Leukemia Cells from Blood Using Interdigitated Microelectrodes," J. Phys. D: Appl. Phys. 27 (1994) 2659]. In addition, they have demonstrated the use of DEP to concentrate DNA in specified regions. In other work, a Japanese group has demonstrated manipulation of DNA in solution [Morishima et al., "Microflow System and Transportation of DNA Molecule by Dielectrophoretic Force Utilizing the Conformal Transition if the Higher Structure of DNA Molecule", IEEE 0-7803-3744-1, 1997].

Such DEP separation process as involve applying an alternating electric field through a series of interdigitated electrodes. By choosing an appropriate excitation frequency, specific cells or particles (DNA in our case) become trapped in the high field gradient regions at the electrode tips. Other particles can then be flushed out of the system, leaving the attracted particles of interest behind for subsequent collection. The University of Texas group has demonstrated this procedure for the removal of human leukemia cells(x) from blood (o) as in FIG. 2 [F. F. Becker, X.-B. Wang, Y. Huang, R. Pethig, J. Vykoukal, and P. R. C. Gascoyne, "The Removal of Human Leukemia Cells from Blood Using Interdigitated Microelectrodes," J. Phys. D: Appl. Phys. 27 (1994) 2659].

SUMMARY OF THE INVENTION

It is an object of this invention to detect and identify biological agents.

It is a further object of this invention to assist in mapping the human genome and other genetic-based biomedical assays by allowing a fully automated microsystem based on microelectromechanical systems (MEMS).

It is still another object of this invention to detect hazardous bacteria in agricultural products and prepared food.

BRIEF DESCRIPTION OF THE DRAWINGS

FIG. 1 PCR Sample Preparation Procedures.

FIGS. 2A and 2B Sequential events for separation of human leukemia cells (HL-60) and normal blood cells.

FIG. 2A mixture of HL-60 and normal blood cells prior to application of an electric field.

FIG. 2B Cancer cells were retained at the electrode tips and normal blood cells eluted from the chamber when the applied electric field was repetitively swept between 20 and 80 kHz and fluid flow was started (picture shown after 20 min.). Cancer cells were retained with a small proportion of the normal blood cells.

FIG. 3B Top view of gapped electrodes on a small footprint substrate wafer.

Figure 3A:
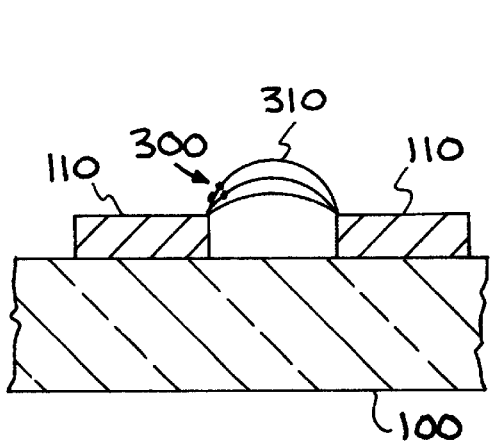
FIG. 3A Dielectrophoretic capture of B.g. spores 300 along the electrode edges.
Figure 3B:
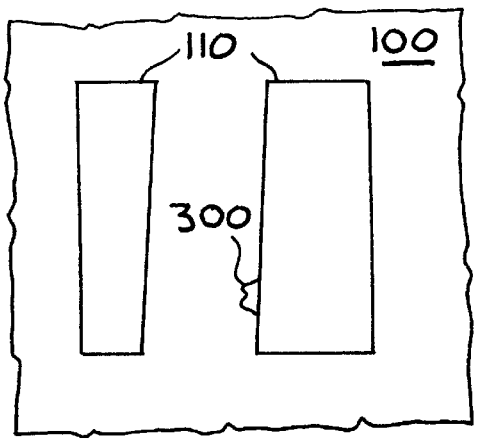
Figure 4:
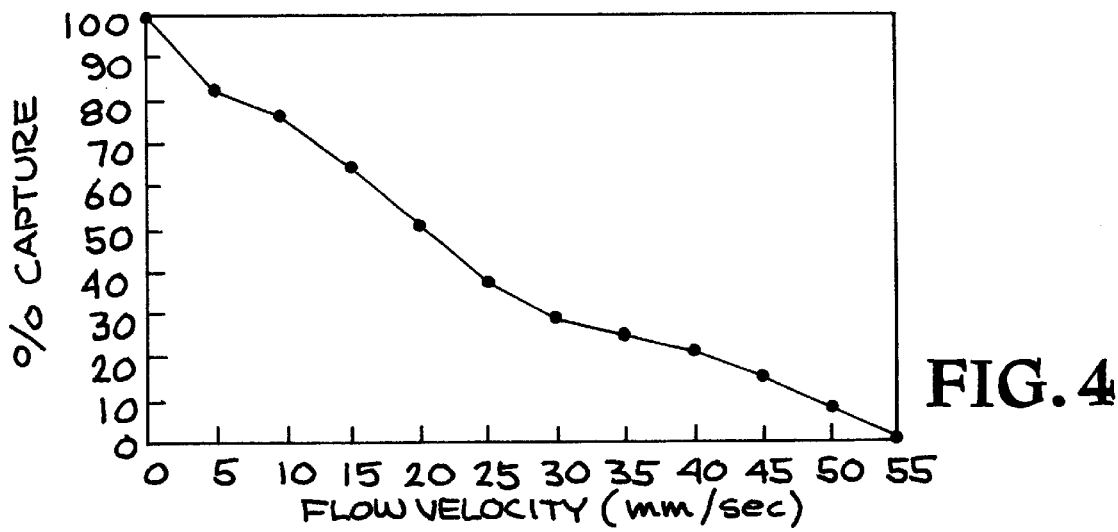
FIG. 4 Approximate percentage of B.g. particles captured from flowing water.
Figure 5:
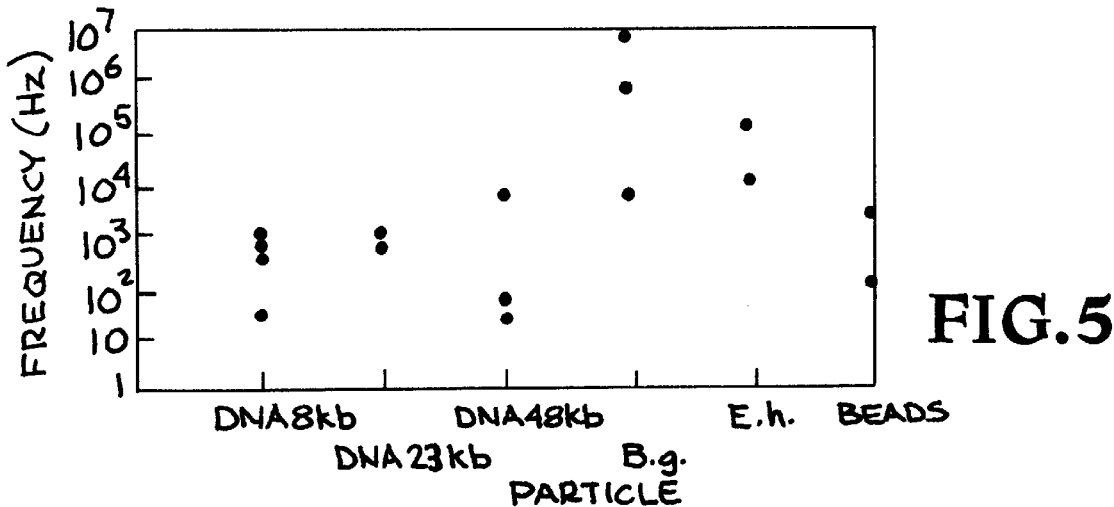
FIG. 5 Frequencies at which positive DEP was observed for particles in water.
Figure 6:
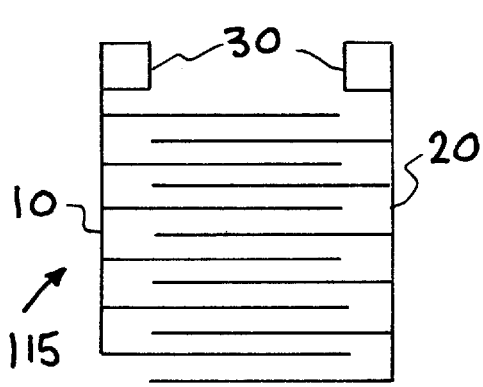
FIG. 6 Interdigitated electrode photolithography pattern.
Figure 7:
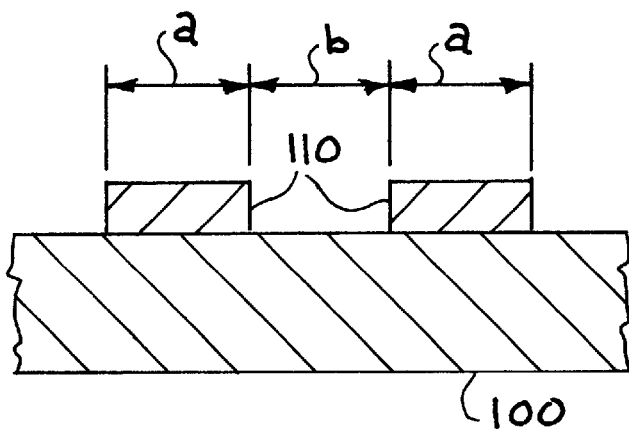
FIG. 7 Interdigitated electrode pattern cross section showing electrode spacings on a substrate wafer.
Figure 8:
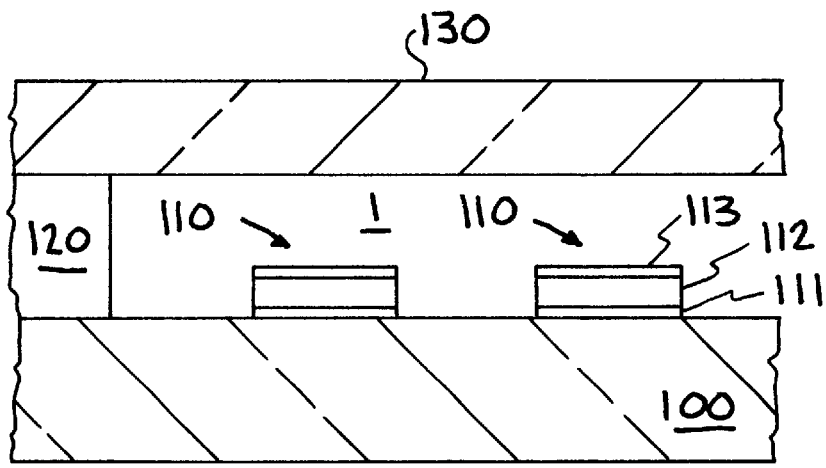
FIG. 8 Interdigitated electrode pattern cross section showing shim and standard microscope cover slip.
Figure 9:
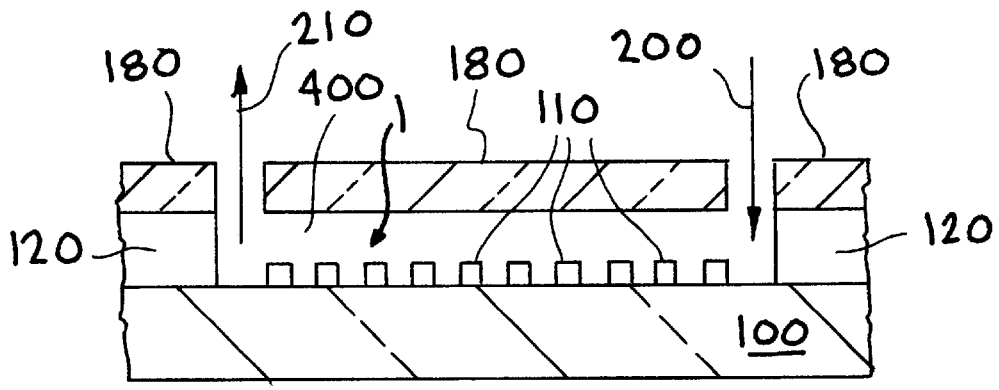
FIG. 9 Interdigitated electrode pattern cross section showing shim, additional glass wafer, and drilled hole for bulk sample fluid access.

FIG. 10 Cutaway perspective view of the interdigitated electrode pattern, shims, additional glass wafer, and drilled hole for bulk sample fluid access.

DETAILED DESCRIPTION OF THE INVENTION

Dielectrophoresis is a highly useful mechanism for a microfluidic DNA sample collection and preparation system. The system is based on the polymerase chain reaction (PCR) technique for amplifying DNA samples. Microelectromechanical systems (MEMS) technology is used to provide complete integration of sample disruption, separation, concentration, and mixing with reagents so that the mixture may be presented to a PCR instrument for analysis.

Several steps are involved in sample preparation as shown in FIG. 1. The steps include:

(1) collection of the sample by any conventional means as from, for instance, an aerosol sampler (step 11), (2) possible, if necessary, (optional) separation of biological from nonbiological material (step 13), (3) disruption of spores such as by mechanical and chemical means (step 15), (4) separation (optionally lysing) and concentration of targeted materials such as DNA from other materials including proteins, RNA and potential interference sources of PCR (step 17), (5) addition of PCR master mix to the extracted DNA which includes specific primers and probes, and non-specific reagents such as PCR buffer, dNTPs, $MgCl_2$, and DNA polymerase enzyme (step 19), and (6) final assay (step 21).

In the microdevices and microfluidic systems of the invention, dielectrophoresis can be applied, particularly in step 17, as a means of separating the DNA from other particles in the solution, such as disrupted spores, smoke, dust, pollen, and any proteins, i.e., contaminants, which may inhibit the PCR reaction. Other targeted materials separated and concentrated by the method and device of the invention include *Bacillus globigii* spores, *Erwinia herbicola* bacteria, spores, bacteria, and polystyrene beads.
Figure 10:
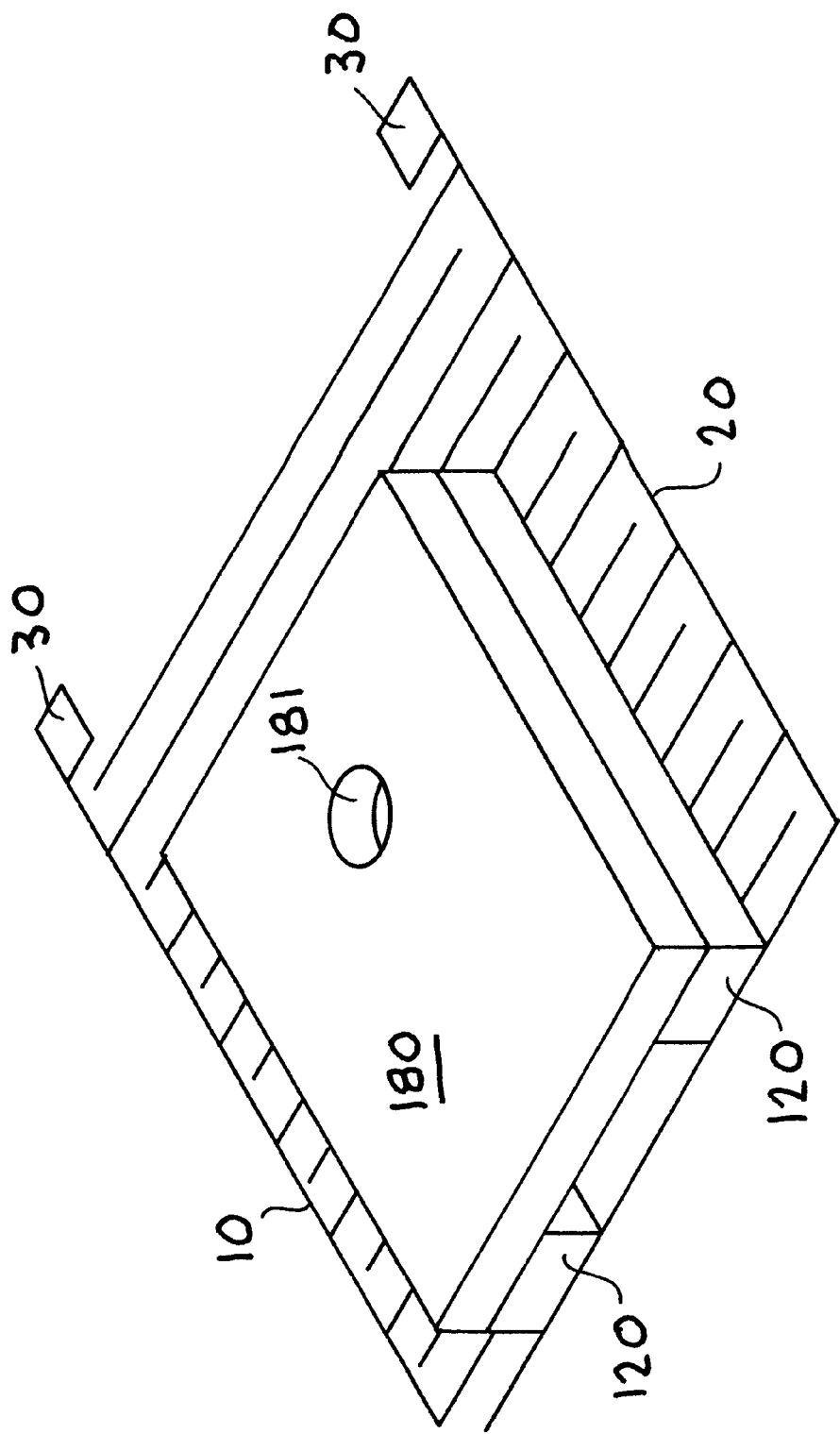

Current technologies for DNA extraction are time consuming, inefficient, and involve multiple steps. The multistep procedures include mixing various solutions such as organic solvents, as well as centrifugation. The present method allows for fully automated microfluidic systems, which are amenable to use by unskilled personnel in the field. Microdevices typically have a relatively small footprint such as capable of sampling volumes of fluids on the order of less than 1000 microliters, and often less than 100 microliters, and even on the order of less than 25 microliters. Furthermore, the surface dimensions can be less than 10 square inches and often less than 5 square inches, while the overall device dimensions can be less than 10 cubic inches, normally less than 5 cubic inches and in some highly preferred embodiments, less than about 1 square inch.

Simple Microfluidic Sample Capture Device

The microdevice is fabricated using standard photolithographic methods. Photoresist is spun on non-conductive materials, such as Pyrex (glass) wafer 100 in FIGS. 3 and 7–9, for example, at 2100 rpm. The resist is photolithographically patterned for interdigitated electrodes as shown in FIG. 6 with 50 micron wide electrodes and 30 micron wide gaps, although gaps (as shown in FIG. 7 as gap width a on glass wafer 100) from about 2–50 micron are useful and electron widths (shown as b in FIG. 7) up to about 100 microns are effective. For example, the electrodes are about 2.2 cm long such that the entire patterned structure covers an area of 2.2 by 2.2 cm to fit a cover, such as a standard microscope slip cover, for optical tests. The electrodes 110 attached to the substrate 100, as shown in the Figures, can contain electrically conductive materials, such as a layer of chromium 111, (e.g., 20 nm of chromium), under a layer of gold 111, (e.g., 200 microns of gold).

A feature of the invention is a thin layer 113 of relatively non-conductive material on the outer surface of the electrode 110 that reduces or essentially prevents undesirable particles and/or molecules from sticking to the electrode outer surface during operation. Such thin non-conductive layers typically have resistivities greater than $\mathbf{10}^5$ ohm-cm, and usually greater than $\mathbf{10}^6$ ohm-cm. Normally the thickness of the outer layer 113 is less than about 1000 angstroms, and often in the range from about 300 to about 500 angstroms. Examples of such non-conductive materials include ceramics and polymeric materials that can be coated on the electrode by such methods as CVD or evaporative or sputtering techniques. Outer electrode layers can have a dielectric constant of greater than about 50, usually above that of water at 80. Highly prefered outer electrode layers include silicon nitride or silicon carbide. Leads may be soldered to the electrodes.

In a batch mode, FIG. 8 depicts a specimen (e.g., bulk sample) 1 containing targeted and contaminant materials (not shown), placed on and/or between electrodes 110 . The bulk sample can be less than 1000 microliters, and can be less than 100 microliters. A cover slip, such as a standard microscope cover slip 130, is applied. An amplified AC voltage is applied between the electrodes, and visual observation through a microscope or other magnification means can be used to determine trapping of the biological particles on the electrode surface. A typical specimen can contain 10 microliters of DNA in concentrations of 500 micrograms/ml and stained using 1 microliter of 1 mM YOYO- I dye from Molecular Probes diluted 10:1 and B.g. in varying concentrations.

Separation means, such as a shim 120 typically comprising wax or plastic, is placed between the Pyrex wafer 100 and the cover slip 130 to determine how far above the surface the dielectrophoretic force can extend. Shims providing predetermined dimensions of about 10 to about 150 microns, e.g., of 12, 25, 50, 75, 100 microns, may be used. It has been found that the DNA can be focused using DEP up to about 25 microns above the electrode surface except in the case of the longer lengths (23 Kbp and 47 Kbp) of DNA at frequencies usually below 1,000, or below 500 Hz in deionized water.

After several minutes of working with B.g., the DEP force can decrease, often due to a build-up of organic material. The wafer surface 100 and/or portions of the electrode 110 can be rejuvenated, such as by exposure of the specimen-contacting portions of the device to oxygen plasma etch for sufficient time, e.g., 2 minutes, to rejuvenate the surface.

A Microfluidic DNA Sample Capture Device

Trapping of moving particles may be performed using a similar process. Here, electrodes are photolithographically patterned on the 4 inch glass wafer such as that shown in FIGS. 6–10. A thin silicon nitride layer 300–500 A is used on electrodes to prevent particles from sticking. Thicker coatings effectively absorb the electric field, thus decreasing the efficiency of the dielectrophoretic force. Thin layers of many different kinds of dielectrics such as silicon oxide or teflon or parylene are also useful. A thin parylene layer over the electrodes was tested and did allow for focusing of B.g. but the B.g. was found to stick to thin material. The thin layers may be as thick as 2000 Angstroms depending on the field applied. The electrodes were 30 microns wide with 30 micron gaps and about 1 cm long to cover approximately a 1 $cm^2$ area. Flow channels are created by cutting the desired channels of roughly 0.5 cm width in a sheet of wax film. The film is sandwiched between the patterned glass wafer and an additional glass wafer with holes drilled into in for fluid access to the channels. For instance in FIG. 9, the assembly is placed within a fixture which provides an interface to external syringe pumps to deliver a specimen 1 flowing (depicted at 200) into a bulk sample channel 400 surrounding electrodes 110. Spring-loaded pogo pins that are soldered into a PC board can be used to provide the electrical connections to the patterned electrodes. An AC signal of varying frequency and voltage is placed on the particles as they are forced through the channel 400 at a rate determined by the syringe pump and exit (depicted at 210). Observation through the microscope, or other detection means, may be used to determine the approximate number of particles that adhere to the electrodes. At predetermined time intervals, the electric field may be removed to determine the numbers of particles trapped in the field versus the number which may have adhered to the surface through molecular interactions.

Changes and modifications in the specifically described embodiments can be carried out without departing from the scope of the invention which is intended to be limited only by the scope of the claims.

We claim:

1. A method of separating a target material comprising the steps of:

a. flowing a bulk sample comprising target material and contaminant material through a microdevice;

b. exerting a dielectrophoretic force upon said bulk sample within the microdevice to selectively separate said target material from said contaminant material, said target material adhering to a dielectric outer layer of an electrode contained in said microdevice, and said dielectric outer layer having a thickness of less than about 2000 angstroms.

2. The method of claim 1 where said target material is selected from the group consisting of DNA, spores, bacteria, and polystyrene beads.

3. The method of claim 2 wherein said spores comprise *Bacillus globigii* spores, and said bacteria comprose *Erwinia herbicola* bacteria.

4. A microfluidic DNA sample preparation method including the steps of:
 (a) separating DNA by dielectrophoretic forces from a bulk sample containing DNA and other materials, said DNA adhering to a dielectric outer layer of thickness less than 1000 angstroms of an electrode exerting said dielectrophoretic forces, and (b) concentrating said DNA from said other materials in said bulk sample to form an extracted DNA.

5. The microfluidic DNA sample preparation method of claim 4, wherein said separating step (a) is performed using dielectrophoresis (DEP) to selectively capture said DNA up to 25 microns above said outer layer of said electrode at frequencies below 1000 Hz.

6. A microfluidic DNA sample preparation device comprising:
 a. a glass wafer substrate;
 b. an interdigitated electrode set patterned on said glass wafer substrate, said electrode set comprising electrodes having a dielectric outer layer of thickness less than 1000 angstroms;
 c. means for applying an alternating voltage to said interdigitated electrode set;
 d. Separation means having a thickness of about 10 to about 15 microns placed over said electrode set; and
 e. an additional wafer substrate placed over said separation means, and
 wherein a first orifice for fluid access, and a second orifice for fluid access is contained on said first substrate and/or on said additional wafer substrate.

7. The device of claim 6 wherein said first orifice is positioned perpendicularly to the interdigitations of said electrode set, and electrode set is capable of collecting a target portion of DNA on said dielectric outer layer of said electrode.

8. An electrode set comprising:
 a. a left electrode set;
 b. a right electrode set; and
 c. an electrical connection to each of the two electrode sets;
 wherein the two electrode sets form an interdigitated pattern of about 10 to 150 micron widths and spaces and comprise electrodes constructed to apply alternating current (AC), said electrodes comprising a dielectric outer layer of thickness less than about 2000 angstroms.

9. The electrode set of claim 8 wherein said electrodes further comprise:
 a. a glass wafer substrate;
 b. a first conductive layer placed on a top surface of the glass wafer substrate;
 c. a second conductive layer placed on the first conductive layer; and
 d. a thin layer of said dielectric outer layer placed on the second conductive layer.

10. The method of claim 1 wherein said target material adhering on said dielectric outer layer for a predetermined interval.

11. The method of claim 10 wherein said target material comprises DNA.

12. The method of claim 4 further comprising (c) adding a polymerase chain replication (PCR) master mix to said extracted DNA.

13. The method of claim 12 wherein said other materials are selected from the group consisting of proteins, RNA, and interference sources of PCR.

14. The set of claim 9 wherein said dielectric is selected from the group consisting of silicon nitride, silicon carbide, paralene, Teflon, and silicon oxide.

15. The set of claim 8 wherein said dielectric outer layer has a dielectric constant of at least 50.

16. The method of claim 4 wherein said DNA adhering on said dielectric outer layer for a predetermined interval.

17. The method of claim 1 wherein said dielectric outer layer has a thickness of about 300 to about 500 angstroms.

18. The method of claim 4 wherein said dielectric outer layer has a thickness of about 300 to about 500 angstroms.

19. The device of claim 6 wherein said dielectric outer layer has a thickness of about 300 to about 500 angstroms.

20. The set of claim 8 wherein said dielectric outer layer has a thickness of about 300 to about 500 angstroms.

* * * * *